(12) United States Patent
Moran

(10) Patent No.: US 6,566,395 B1
(45) Date of Patent: May 20, 2003

(54) METHODS OF TREATING PROLIFERATIVE DISORDERS

(75) Inventor: Stanford Mark Moran, Orinda, CA (US)

(73) Assignee: BioMedicines, Inc., Alameda, CA (US)

(*) Notice: Subject to any disclaimer, the term of this patent is extended or adjusted under 35 U.S.C. 154(b) by 0 days.

(21) Appl. No.: 09/577,689

(22) Filed: May 22, 2000

Related U.S. Application Data

(60) Provisional application No. 60/135,995, filed on May 25, 1999.

(51) Int. Cl.[7] ............................................. A61K 31/275
(52) U.S. Cl. ......................................... 514/521
(58) Field of Search ........................................ 514/521

(56) References Cited

U.S. PATENT DOCUMENTS

| | | |
|---|---|---|
| 4,284,786 A | 8/1981 | Kammerer et al. |
| 4,351,841 A | 9/1982 | Kammerer et al. |
| 5,240,960 A | 8/1993 | Hambleton et al. |
| 5,384,423 A | 1/1995 | Hambleton et al. |
| 5,700,822 A | 12/1997 | Hirth et al. |
| 5,700,823 A | 12/1997 | Hirth et al. |
| 5,721,277 A | 2/1998 | Tang |

FOREIGN PATENT DOCUMENTS

WO    95/19169    7/1995

OTHER PUBLICATIONS

Goodman &Gilman, Pharmacological Basis of Therapeutics, Ninth Edition, Chapter 52, pp. 1291–1304 (1996).*

* cited by examiner

*Primary Examiner*—Dwayne C. Jones
*Assistant Examiner*—C. Delacroix-Muirheid
(74) *Attorney, Agent, or Firm*—Burns, Doane, Swecker & Mathis LLP

(57) ABSTRACT

Disclosed are methods and compositions for treating proliferative disorders, such as cancers, blood vessel disorders, fibrotic disorders and acute or chronic rejection of transplanted organs, tissue or cells, using compounds of formula I or a tautomeric isomer thereof:

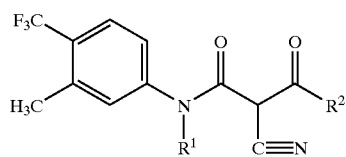

wherein $R^1$ and $R^2$ are as defined; or a pharmaceutically-acceptable salt or pro-drug thereof.

17 Claims, No Drawings

METHODS OF TREATING PROLIFERATIVE DISORDERS

CROSS REFERENCE TO RELATED APPLICATION

This application claims priority under 35 USC 119(e) to U.S. provisional application Serial No. 60/135,995, filed on May 25, 1999, the disclosure of which is incorporated by reference in its entirety.

BACKGROUND OF THE INVENTION

1. Field of the Invention

This invention relates to methods and compositions for treating proliferative disorders, such as cancers, blood vessel disorders and fibrotic disorders, using N-(3-methyl-4-trifluoromethylphenyl) 2-cyano-2-(cycloalkylcarbonyl)acetamide compounds or pharmaceutical compositions comprising such compounds.

2. References

The following publications, patents and patent applications are cited in this application as superscript numbers:

1. U.S. Pat. No. 4,284,786, issued Aug. 18, 1981, to Kammerer et al.
2. U.S. Pat. No. 4,351,841, issued Sep. 28, 1982, to Kammerer et al.
3. U.S. Pat. No. 5,700,822, issued Dec. 23, 1997, to Hirth et al.
4. U.S. Pat. No. 5,700,823, issued Dec. 23, 1997, to Hirth et al.
5. U.S. Pat. No. 5,721,277, issued Feb. 24, 1998, to Tang.
6. International Publication No. WO 95/19169, published Jul. 20, 1995.
7. U.S. Pat. No. 5,240,960, issued Aug. 31, 1993, to Hambleton et al.
8. U.S. Pat. No. 5,384,423, issued Jan. 24, 1995, to Hambleton et al.

Each of the publications, patents and patent applications referred to in this application, including those listed above, are herein incorporated by reference in their entirety to the same extent as if each individual publication, patent or patent application was specifically and individually indicated to be incorporated by reference in its entirety.

3. State of the Art

Proliferative growth of cells, tissues and organs occurs in various mammalian disorders, such as cancers, blood vessel disorders and fibrotic disorders. The compounds leflunomide (also known as 5-methylisoxazole-4-carboxylic acid-(4-trifluromethyl)-anilide) and N-(4-trifluoromethylphenyl)-2-cyano-3-hydroxycrotonamide have been reported to be useful in inhibiting hyper-proliferative cell growth. Leflunomide reportedly acts as a pro-drug for the in vivo formation of N-(4-trifluoromethylphenyl)-2-cyano-3-hydroxycrotonamide. See, for example, U.S. Pat. No. 4,284,786[1] and U.S. Pat. No. 4,351,841.[2] Other compounds reportedly useful for the treatment of cell proliferation disorders are disclosed in U.S. Pat. No. 5,700,822;[3] U.S. Pat. No. 5,700,823;[4] U.S. Pat. No. 5,721,277;[5] and International Publication No. WO 95/19169.[6]

U.S. Pat. No. 5,240,960[7] and U.S. Pat. No. 5,384,423[8] disclose various N-(substituted phenyl) 2-cyano-2-(cycloalkylcarbonyl)acetamide compounds and methods for treating inflammation in warm-blooded animals using such compounds.

Surprisingly, it has now been discovered that certain N-(substituted phenyl) 2-cyano-2-(cycloalkylcarbonyl) acetamide compounds, i.e., those having a 3-methyl-4-trifluoromethylphenyl group, are also useful for the treatment of proliferative disorders, such as cancers, blood vessel disorders, fibrotic disorders and the rejection of transplanted organs, tissues and cells.

SUMMARY OF THE INVENTION

The present invention is directed to methods and compositions for treating proliferative disorders using N-(3-methyl-4-trifluoromethylphenyl) 2-cyano-2-(cycloalkylcarbonyl)acetamide compounds or pharmaceutical compositions comprising such compounds.

Accordingly, in one of its method aspects, the present invention provides a method of treating a cell, tissue or organ with a proliferative disorder comprising administering to said cell, tissue or organ a proliferation-inhibiting amount of a compound of formula I or a tautomeric isomer thereof:

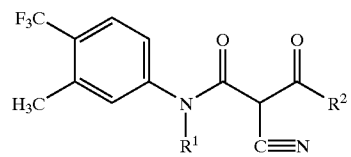

I wherein
$R^1$ is hydrogen or alkyl of from 1 to 3 carbon atoms;
$R^2$ is cycloalkyl or substituted cycloalkyl having from 3 to 6 carbon atoms in the cycloalkyl ring; or a pharmaceutically-acceptable salt or pro-drug thereof; and
further wherein the proliferation-inhibiting amount provides a concentration of the compound of formula I in the cell, tissue or organ which inhibits the proliferative disorder.

Preferably, in the methods of this invention, $R^1$ in formula I is hydrogen or methyl. More preferably, $R^1$ is hydrogen. $R^2$ in formula I is preferably cyclopropyl, cyclobutyl or cyclopentyl. More preferably, $R^2$ is cyclopropyl. In a particularly preferred embodiment, $R^1$ is hydrogen and $R^2$ is cyclopropyl.

Preferably, the proliferation-inhibiting amount employed in the above method provides a concentration of the compound of formula I in the cell, tissue or organ from about 0.1 μg/mL to about 1000 μg/mL.

In another of its method aspects, the present invention provides a method of treating a mammal having a proliferative disorder comprising administering to said mammal a proliferation-inhibiting amount of a compound of formula I or a tautomeric isomer thereof:

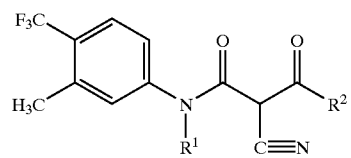

I wherein
$R^1$ is hydrogen or alkyl of from 1 to 3 carbon atoms; and
$R^2$ is cycloalkyl or substituted cycloalkyl having from 3 to 6 carbon atoms in the cycloalkyl ring; or a pharmaceutically-acceptable salt or pro-drug thereof.

Preferably, the proliferation-inhibiting amount of the compound of formula I ranges from about 0.001 mg/kg/day to about 2000 mg/kg/day; more preferably, from about 0.01 mg/kg/day to about 1000 mg/kg/day, and still more preferably, from about 1 mg/kg/day to about 1000 mg/kg/day.

In a preferred embodiment of the methods of this invention, the proliferative disorder being treated by the compounds of formula I is a cancer; preferably, a solid tumor cancer, a bone marrow cell cancer or lymphatic or lymph node-related cancer; more preferably, a solid tumor cancer, or lymphatic or lymph node-related cancer.

In other preferred embodiments of this invention, the proliferative disorder being treated is a blood vessel proliferative disorder or a fibrotic disorder.

In yet another preferred embodiment of this invention, the proliferative disorder being treated is the acute or chronic rejection of a transplanted organ, tissue or cell.

In the methods of this invention, the compound of formula I is preferably administered orally, intravenously, parenterally or transdermally.

In one embodiment of this invention, the compounds of formula I are administered in a manner to establish an adequate plasma level of the compound of formula I in the mammal being treated. In this embodiment, a compound of formula I is administered to said mammal in a dosing cycle comprising the steps of:

(a) administering to the mammal a first proliferation-inhibiting amount for a period of 1 to 21 days; and then (b) administering to the mammal a second proliferation-inhibiting amount for a period of 1 to 21 days, wherein said second proliferation-inhibiting amount is the same or different from said first proliferation-inhibiting amount.

If desired, this dosing cycle can optionally further comprise a non-dosing period of from 1 to 21 days between step(a) and step (b).

Preferably, the ratio of the second proliferation-inhibiting amount to the first proliferation-inhibiting amount ranges from about 1:1 to about 1:6, and if a reduction in ratio below 1:1 is required, then more preferably, from about 2:6 to about 4:6. This treatment regime may be repeated any number of times to establish and/or maintain an adequate plasma level of the compound of formula I in the mammal being treated, i.e., a plurality of such dosing cycles can be administered to the mammal.

The compounds of formula I may be administered to a mammal with a proliferative disorder before, after or in conjunction with other chemotherapeutic agents or with other therapy intended to modulate, to suppress or to stimulate the mammal's immune system. Additionally, the compounds of formula I can be administered before, in conjunction with, or after other conventional methods for treating proliferative disorders, such as radiation therapy, ablative or partially ablative surgical procedures or a bone marrow transplant, which themselves may be employed in conjunction with chemotherapeutic agents or with other therapy intended to modulate, suppress or stimulate the mammal's immune system.

When administered with another chemotherapeutic agent or agents, each chemotherapeutic agent is preferably independently selected from the group consisting of androgens, asparaginase, azathioprine, 5-azacitidine, BCG, bleomycin, busulfan, carbetimer, carboplatin chlorambucil, cisplatin, corticosteroids, cyclophosphamide, cytarabine, dacarbazine, dactinomicin, daunomycin, doxorubicin, epirubicin, estrogens, etoposide, fadrazole, 5-flurouracil, gemcitabine, hydroxyurea, ifosfamide, interferon alpha, interferon beta, interferon gamma, an interleukin, isotretinoin, lomustine, melphalan, 6-mercaptopurine, methotrexate, mitomycin-c, mitotane, mitoxantrone, paclitaxel, pentostatin, procabazine, progestins, rituximab, streptozocin, tamoxifen, toxotere, teniposide, thioguanine, thiotepa, topotecan, toremifene, tretinoin, uracil mustard, vinblastine, vincristine and vinorelbine; or other drugs intended to affect or alter, directly or indirectly, the replication or functioning of cellular deoxyribonucleic acid or cellular ribonucleic acid, or other drugs intended to affect or alter, directly or indirectly, the functioning of the immune system.

When the proliferative disorder being treated is acute or chronic rejection of a transplanted organ, tissue or cell, the compound of formula I may be administered in combination with one or more immunosuppressive agents. Preferably, each immunosuppressive agent is independently selected from the group consisting of azathioprine, corticosteroids, cyclosporin, cyclophosphamide, mycophenolic acid or congeners thereof, monoclonal or polyclonal antibodies, or other agents or procedures used to prevent, suppress or reverse rejection of a transplanted organ, tissue or cell.

Accordingly, in one of its composition aspects, this invention provides a pharmaceutical composition or admixture comprising:

(a) about 1 to about 99 weight percent of a first composition comprising a compound of formula I or a tautomeric isomer thereof:

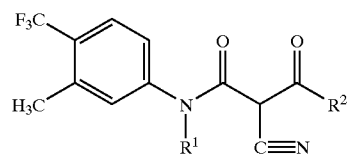

I wherein $R^1$ is hydrogen or alkyl of from 1 to 3 carbon atoms; and $R^2$ is cycloalkyl or substituted cycloalkyl having from 3 to 6 carbon atoms in the cycloalkyl ring; or a pharmaceutically-acceptable salt or pro-drug thereof;

(b) about 1 to about 99 weight percent of a second composition comprising one or more chemotherapeutic agents, or one or more immunosuppressive agents; and (c) from 0 to about 98 weight percent of a pharmaceutically-acceptable carrier.

Among other properties, the compounds of formula I have been discovered to be particularly useful for treating solid tumors. Accordingly, in a particularly preferred embodiment, the present invention provides a method of inhibiting tumor growth in a mammal having a solid tumor comprising administering to said mammal a tumor growth-inhibiting amount of a compound of formula II or a tautomeric isomer thereof:

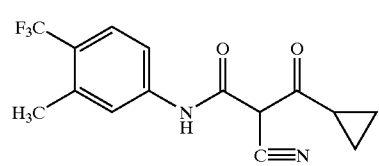

II or a pharmaceutically-acceptable salt or pro-drug thereof.

DETAILED DESCRIPTION OF THE INVENTION

This invention provides methods of treating proliferative disorders using N-(3-methyl-4-trifluoromethylphenyl)

2-cyano-2-(cycloalkylcarbonyl)-acetamide compounds and pharmaceutical compositions comprising such compounds. When describing the methods, compositions and compounds of this invention, the following terms have the following meanings unless otherwise indicated. Those terms not defined have their art-recognized meanings.

Definitions

"Acyl" refers to the group —C(O)$R^a$ where $R^a$ is hydrogen, alkyl, substituted alkyl, alkenyl, substituted alkenyl, alkynyl, substituted alkynyl, cycloalkyl, substituted cycloalkyl, cycloalkenyl, substituted cycloakenyl or aryl.

"Acylamino" refers to the group —N$R^a$C(O)$R^a$ where $R^a$ is hydrogen, alkyl, substituted alkyl, alkenyl, substituted alkenyl, alkynyl, substituted alkynyl, cycloalkyl, substituted cycloalkyl, cycloalkenyl, substituted cycloakenyl or aryl.

"Acyloxy" refers to the group —OC(O)$R^a$ where $R^a$ is hydrogen, alkyl, substituted alkyl, alkenyl, substituted alkenyl, alkynyl, substitued alkynyl, cycloalkyl, substituted cycloalkyl, cycloalkenyl, substituted cycloakenyl or aryl.

"Alkenyl" refers to monovalent branched or unbranched hydrocarbon groups preferably having from 2 to 10 carbon atoms and more preferably 2 to 6 carbon atoms and having at least 1 and preferably from 1–2 sites of alkenyl unsaturation. Representative alkenyl groups include ethenyl (—CH=$CH_2$), n-propenyl (—$CH_2$CH=$CH_2$), isopropenyl (—C($CH_3$)=$CH_2$) and the like.

"Substituted alkenyl" refers to an alkenyl group having 1 to 5 substituents, and preferably 1 to 3 substituents, selected from the group consisting of acyl, acylamino, acyloxy, alkoxy, alkoxycarbonyl, alkoxycarbonylamino, amino, substituted amino, aminocarbonyl, aminocarbonylamino, aminocarbonyloxy, aryl, aryloxy, aryloxycarbonyl, aryloxycarbonylamino, carboxyl, cyano, cycloalkyl, cycloalkenyl, halogen, hydroxy, nitro, oxo, sulfo, sulfonamide, thiol, thioalkoxy, thioaryloxy, thiooxo, trifluoromethyl, trifluoromethoxy, —SO-alkyl, —SO-substituted alkyl, —SO-aryl, —$SO_2$-alkyl, —$SO_2$-substituted alkyl and —$SO_2$-aryl.

"Alkoxy" refers to the group —O$R^b$ where $R^b$ is alkyl or substituted alkyl. Representative alkoxy groups include, by way of example, methoxy, ethoxy, n-propoxy, isopropoxy, n-butoxy, tert-butoxy, sec-butoxy, n-pentyloxy, n-hexyloxy, and the like.

"Alkoxycarbonyl" refers to the group —C(O)O$R^c$ where $R^c$ is alkyl, substituted alkyl, alkenyl, substituted alkenyl, alkynyl, substituted alkynyl, cycloalkyl, substituted cycloalkyl, cycloalkenyl or substituted cycloalkenyl.

"Alkoxycarbonylamino" refers to the group —N$R^a$C(O)O$R^c$ where $R^a$ is hydrogen, alkyl, substituted alkyl, alkenyl, substituted alkenyl, alkynyl, substituted alkynyl, cycloalkyl, substituted cycloalkyl, cycloalkenyl, substituted cycloakenyl or aryl; and $R^c$ is alkyl, substituted alkyl, alkenyl, substituted alkenyl, alkynyl, substituted alkynyl, cycloalkyl, substituted cycloalkyl, cycloalkenyl and substituted cycloalkenyl.

"Alkyl" refers to monovalent branched or unbranched hydrocarbon groups preferably having from 1 to about 10 carbon atoms, more preferably 1 to 8 carbon atoms and still more preferably 1 to 6 carbon atoms. This term is exemplified by groups such as methyl, ethyl, n-propyl, isopropyl, n-butyl, isobutyl, lert-butyl, n-hexyl, n-octyl and the like. The term "lower alkyl" refers to alkyl groups having 1 to 6 carbon atoms.

"Substituted alkyl" refers to an alkyl group having from 1 to 5 substituents, and preferably 1 to 3 substituents, selected from the group consisting of acyl, acylamino, acyloxy, alkoxy, alkoxycarbonyl, alkoxycarbonylamino, amino, substituted amino, aminocarbonyl, aminocarbonylamino, aminocarbonyloxy, aryl, aryloxy, aryloxycarbonyl, aryloxycarbonylamino, carboxyl, cyano, cycloalkyl, cycloalkenyl, halogen, hydroxy, nitro, oxo, sulfo, sulfonamide, thiol, thioalkoxy, thioaryloxy, thiooxo, trifluoromethyl, trifluoromethoxy, —SO—$R^c$ and —$SO_2$—$R^c$, where $R^c$ is alkyl, substituted alkyl, alkenyl, substituted alkenyl, alkynyl, substituted alkynyl, cycloalkyl, substituted cycloalkyl, cycloalkenyl and substituted cycloalkenyl.

"Alkynyl" refers to monovalent branched or unbranched hydrocarbon groups preferably having from 2 to 10 carbon atoms and more preferably 2 to 6 carbon atoms and having at least 1 and preferably from 1–2 sites of alkynyl unsaturation. Representative alkynyl groups include ethynyl (—C≡CH), propargyl (—$CH_2$C≡CH), and the like.

"Substituted alkynyl" refers to an alkynyl group having from 1 to 5 substituents, and preferably 1 to 3 substituents, selected from the group consisting of acyl, acylamino, acyloxy, alkoxy, alkoxycarbonyl, alkoxycarbonylamino, amino, substituted amino, aminocarbonyl, aminocarbonylamino, aminocarbonyloxy, aryl, aryloxy, aryloxycarbonyl, aryloxycarbonylamino, carboxyl, cyano, cycloalkyl, cycloalkenyl, halogen, hydroxy, nitro, oxo, sulfo, sulfonamide, thiol, thioalkoxy, thioaryloxy, thiooxo, trifluoromethyl, trifluoromethoxy, —SO—$R^c$ and —$SO_2$—$R^c$, where $R^c$ is alkyl, substituted alkyl, alkenyl, substituted alkenyl, alkynyl, substituted alkynyl, cycloalkyl, substituted cycloalkyl, cycloalkenyl and substituted cycloalkenyl.

"Amino" refers to the group —$NH_2$.

"Substituted amino" refers to the group —N$R^a R^a$ where each $R^a$ is independently hydrogen, alkyl, substituted alkyl, alkenyl, substituted alkenyl, alkynyl, substituted alkynyl, cycloalkyl, substituted cycloalkyl, cycloalkenyl, substituted cycloakenyl or aryl, provide both of $R^a$ are not hydrogen.

"Aminocarbonyl" refers to the group —C(O)N$R^a R^a$ where each $R^a$ is independently hydrogen, alkyl, substituted alkyl, alkenyl, substituted alkenyl, alkynyl, substituted alkynyl, cycloalkyl, substituted cycloalkyl, cycloalkenyl, substituted cycloakenyl or aryl.

"Aminocarbonylamino" refers to the group —N$R^a$C(O)N$R^a R^a$ where each $R^a$ is independently hydrogen, alkyl, substituted alkyl, alkenyl, substituted alkenyl, alkynyl, substituted alkynyl, cycloalkyl, substituted cycloalkyl, cycloalkenyl, substituted cycloakenyl or aryl.

"Aminocarbonyloxy" refers to the group —OC(O)N$R^a R^a$ where each $R^a$ is independently hydrogen, alkyl, substituted alkyl, alkenyl, substituted alkenyl, alkynyl, substituted alkynyl, cycloalkyl, substituted cycloalkyl, cycloalkenyl, substituted cycloakenyl or aryl.

"Aryl" refers to an unsaturated aromatic carbocyclic group of from 6 to 14 carbon atoms having a single ring (e.g., phenyl) or multiple condensed rings (e.g., naphthyl or anthryl). Preferred aryls include phenyl, naphthyl and the like. Unless otherwise constrained by the definition for the individual substituent, such aryl groups can optionally be substituted with from 1 to 5 substituents, and preferably 1 to 3 substituents, selected from the group consisting of acyl, acylamino, acyloxy, alkenyl, substituted alkenyl, alkoxy, alkoxycarbonyl, alkoxycarbonylamino, alkyl, substituted alkyl, alkynyl, substituted alkynyl, amino, substituted amino, aminocarbonyl, aminocarbonylamino, aminocarbonyloxy, aryl, aryloxy, aryloxycarbonyl, aryloxycarbonylamino, carboxyl, cyano, cycloalkyl, substituted cycloalkyl, cycloalkenyl, substituted cycloalkenyl, halogen, hydroxy, nitro, sulfo, sulfonamide, thiol, thioalkoxy, thioaryloxy, trifluoromethyl, trifluoromethoxy, —SO—$R^c$ and —$SO_2$—$R^c$, where $R^c$ is alkyl, substituted alkyl, alkenyl, substituted alkenyl, alkynyl, substituted alkynyl, cycloalkyl, substituted cycloalkyl, cycloalkenyl and substituted cycloalkenyl.

"Aryloxy" refers to —OR$^d$ wherein R$^d$ is aryl.

"Aryloxycarbonyl" refers to —C(O)OR$^d$ wherein R$^d$ is aryl.

"Aryloxycarbonylamino" refers to —NR$^a$C(O)OR$^c$ where R$^a$ is hydrogen, alkyl, substituted alkyl, alkenyl, substituted alkenyl, alkynyl, substituted alkynyl, cycloalkyl, substituted cycloalkyl, cycloalkenyl, substituted cycloakenyl or aryl, and R$^d$ is aryl.

"Carboxyl" refers to the group —C(O)OH.

"Cyano" refers to the group —CN.

"Cycloalkyl" refers to cyclic alkyl groups of from 3 to 10 carbon atoms having a single cyclic ring or multiple condensed rings, including fused and bridged ring systems, which can be optionally substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, or multiple ring structures such as adamantanyl, and the like.

"Substituted cycloalkyl" refers to a cycloalkyl group having from 1 to 5 substituents, and preferably 1 to 3 substituents, selected from the group consisting of acyl, acylamino, acyloxy, alkoxy, alkoxycarbonyl, alkoxycarbonylamino, amino, substituted amino, aminocarbonyl, aminocarbonylamino, aminocarbonyloxy, aryl, aryloxy, aryloxycarbonyl, aryloxycarbonylamino, carboxyl, cyano, cycloalkyl, cycloalkenyl, halogen, hydroxy, nitro, oxo, sulfo, sulfonamide, thiol, thioalkoxy, thioaryloxy, thiooxo, trifluoromethyl, trifluoromethoxy, —SO—R$^c$ and —SO$_2$—R$^c$, where R$^c$ is alkyl, substituted alkyl, alkenyl, substituted alkenyl, alkynyl, substituted alkynyl, cycloalkyl, substituted cycloalkyl, cycloalkenyl and substituted cycloalkenyl.

"Cycloalkenyl" refers to cyclic alkenyl groups of from 4 to 10 carbon atoms having a single cyclic ring and at least one point of internal unsaturation which can be optionally substituted with from 1 to 3 alkyl groups. Examples of suitable cycloalkenyl groups include, for instance, cyclopent-3-enyl, cyclohex-2-enyl, cyclooct-3-enyl and the like.

"Substituted cycloalkenyl" refers to a cycloalkenyl group having from 1 to 5 substituents, and preferably 1 to 3 substituents, selected from the group consisting of acyl, acylamino, acyloxy, alkoxy, alkoxycarbonyl, alkoxycarbonylamino, amino, substituted amino, aminocarbonyl, aminocarbonylamino, aminocarbonyloxy, aryl, aryloxy, aryloxycarbonyl, aryloxycarbonylamino, carboxyl, cyano, cycloalkyl, cycloalkenyl, halogen, hydroxy, nitro, oxo, sulfo, sulfonamide, thiol, thioalkoxy, thioaryloxy, thiooxo, trifluoromethyl, trifluoromethoxy, —SO—R$^c$ and —SO$_2$—R$^c$, where R$^c$ is alkyl, substituted alkyl, alkenyl, substituted alkenyl, alkynyl, substituted alkynyl, cycloalkyl, substituted cycloalkyl, cycloalkenyl and substituted cycloalkenyl.

"Halo" or "halogen" refers to fluoro, chloro, bromo and iodo. Preferred halo groups are either fluoro or chloro.

"Hydroxy" refers to the group —OH.

"Keto" or "oxo" refers to the group =O.

"Nitro" refers to the group —NO$_2$.

"Sulfo" refers to the group —SO3H.

"Sulfonamide" refers to the group —SO$_2$NR$^a$R$^a$ where each R$^a$ is independently hydrogen, alkyl, substituted alkyl, alkenyl, substituted alkenyl, alkynyl, substituted alkynyl, cycloalkyl, substituted cycloalkyl, cycloalkenyl, substituted cycloakenyl or aryl.

"Thiol" refers to the group —SH.

"Thioalkoxy" refers to the group —SR$^b$ where R$^b$ is alkyl or substituted alkyl.

"Thioaryloxy" refers to the group —SR$^d$ where R$^d$ is aryl.

"Thioketo" or "thioxo" refers to the group =S.

"Trifluoromethoxy" refers to the group —OCF$_3$.

"Trifluoromethyl" refers to the group —CF$_3$.

"Pharmaceutically acceptable salt" refers to pharmaceutically acceptable salts of a compound of Formula I which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

"Pro-drugs" means any compound which releases a biologically active compound of formula I in vivo when such a pro-drug is administered to a mammalian subject. Pro-drugs of a compound of formula I are prepared by modifying functional groups present in the compound of formula I in such a way that the modifications may be cleaved in vivo to release the parent compound. Pro-drugs include, by way of illustration, compounds wherein a hydroxy, amino, carboxyl, or thiol group is bonded to any group that may be cleaved in vivo to regenerate the free hydroxyl, amino, carboxyl, or thiol group, respectively. Examples of pro-drugs include, but are not limited to esters (e.g., acetate, formate, and benzoate derivatives), amides and the like.

The term "tautomers" or "tautomeric isomers" refers to two of more isomers of a keto compound, i.e. a compound of formula I, which differ only by placement of a proton and the corresponding location of the double bond, i.e., the keto and enol forms of a keto compound. Typically, an equilibrium exists, particularly in solution, between the keto and enol forms of such compounds. For example, the compound of formula II (Laflunimus) can be either in its keto or enol form as shown below:

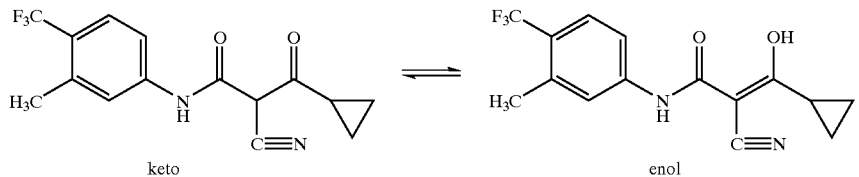

keto  enol

When referring to one form of the compound the other is inclusive of that form. Additionally, it will readily apparent to a person skilled in the art that the relative ratios of the two forms will depend on the environment around the compound such as pH, and the like.

"Treating" or "Treatment" of a Disease Includes:

(1) preventing the disease, i.e. causing the clinical symptoms or signs of the disease not to develop in a mammal that may be exposed to or predisposed to the disease but which does not yet experience or display symptoms or signs of the disease, (2) inhibiting the disease, i.e., arresting or reducing the rate of development of the disease or its clinical symptoms or signs, (3) relieving the disease, i.e., causing partial or complete regression of the disease or its clinical symptoms or signs, (4) a combination of (1), (2) or (3) above encompassing different clinical symptoms or signs.

A "therapeutically effective amount" means the amount of a compound that, when administered to a mammal to treat a disease, is sufficient to effect treatment of the disease. The "therapeutically effective amount" may vary depending on the compound, the disease and its status or severity, the age, weight, other medical conditions, etc., of the mammal to be treated. A "proliferation-inhibiting amount" means an amount of a compound that is sufficient to effect treatment of a proliferative disorder. The therapeutically effective amount may also vary depending upon one or more past or concurrent medical, surgical, or radiation therapy interventions.

Compound Preparation

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Second Edition, Wiley, N.Y., 1991, and references cited therein.

Furthermore, the compounds of this invention may contain one or more chiral centers. Accordingly, if desired, such compounds can be prepared or isolated as pure stereoisomers, i.e., as individual enantiomers or diastereomers, or as stereoisomer-enriched mixtures, or as a racemic mixture. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like. Any and all geometric isomers of the compounds of this invention are also included within the scope of this invention including, for example, cis and trans or E- and Z-isomers.

The compounds of formula I can be prepared using the procedures described, for example, in U.S. Pat. No. 5,240,960, issued Aug. 31, 1993, and U.S. Pat. No. 5,384,423, issued Jan. 24, 1995, the disclosures of which are incorporated herein by reference in their entirety. Specifically, the compounds of formula I may be prepared by reacting a compound of formula III:

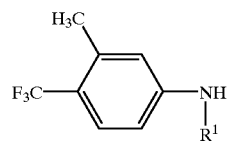

where $R^1$ is as defined herein, with a compound of formula IV:

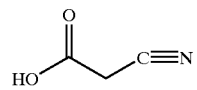

or an acid derivative thereof to form a compound of formula V:

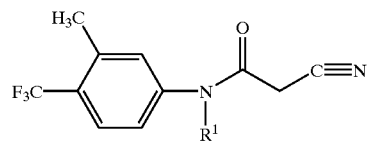

Intermediate V is then reacted with a strong base, such as sodium hydride, optionally in the presence of a catalyst such as imidazole, to form the corresponding anion which is then reacted with a compound of formula VI:

$R^2COHal$      VI where $R^2$ is as defined herein and Hal is a halogen, to provide the compound of formula I.

Compounds of formula III are either commercially available or may be prepared using conventional reagent and procedures from commercially available starting materials. Preferred compounds of formula III include, by way of illustration, 3-methyl-4-trifluoromethylaniline, N-methyl-3-methyl-4-trifluoromethylaniline, N-ethyl-3-methyl-4-trifluoromethylaniline and the like.

Similarly, compounds of formula IV and VI are either commercially available or may be prepared using conventional reagent and procedures from commercially available starting materials. For example, cyanoacetic acid, IV, is commercially available from Aldrich Chemical Company, Milwaukee, Wis. 53201 USA. Preferred compounds of formula VI include, by way of example, cyclopropanecarbonyl chloride (e.g., Aldrich), 2,2,3,3-tetramethyl-cyclopropane-1-carbonyl chloride, cyclobutanecarbonyl chloride (e.g., Aldrich), cyclopentanecarbonyl chloride (e.g., Aldrich), cyclohexanecarbonyl chloride (e.g., Aldrich) and the like.

Preferably, the reaction of the compounds of formulae III and IV is conducted in the presence of diisopropylcarbodiimide or dichlorohexyl-carbodiimide in an anhydrous organic solvent, such as dichloromethane or tetrahydrofuran. A preferred functional derivative of the acid of formula IV is cyanoacetyl chloride prepared in situ from phosphorus pentachloride and cyanoacetic acid.

The reaction of the compound of formula V with sodium hydride is preferably conducted in an anhydrous organic solvent such as tetrahydrofuran. The reaction of the resulting anion of V with a compound of formula VI is preferably conducted in an anhydrous organic solvent such as dichloromethane.

The compounds of formula I have an acidic character and the addition salts of such compounds may be prepared by reacting approximately stoichiometric amounts of a compound of formula I with a base with or without prior isolation of the compound of formula 1.

Pharmaceutical Formulations

When employed in the methods of this invention, the compounds of this invention are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

The pharmaceutical compositions employed in the methods of this invention contain, as the active ingredient, one or more of the compounds of formula I associated with pharmaceutically acceptable carriers. In making the compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of, e.g., less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions can be formulated so as to provide quick, sustained or delayed release of the active ingredient after administration to the patient by employing procedures known in the art.

The compositions are preferably formulated in a unit dosage form, each dosage containing from about 5 to about 1000 mg, more usually about 25 to about 500 mg, and most commonly from about 100 to about 200 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound is effective over a wide dosage range and is generally administered in a pharmaceutically effective amount. It, will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, signs, prior or concurrent medical, surgical, or radiation therapy, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compositions of the present invention may be incorporated for administration orally or by injection include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, preferably orally or nasally, from devices which deliver the formulation in an appropriate manner.

The following formulation examples illustrate the pharmaceutical compositions of the present invention.

FORMULATION EXAMPLE 1

Hard gelatin capsules containing the following ingredients are prepared:

| Ingredient | Quantity (mg/capsule) |
| --- | --- |
| Active Ingredient | 100.0 |
| Starch | 305.0 |
| Magnesium stearate | 5.0 |

The above ingredients are mixed and filled into hard gelatin capsules in 410 mg quantities.

FORMULATION EXAMPLE 2

A tablet formula is prepared using the ingredients below:

| Ingredient | Quantity (mg/tablet) |
| --- | --- |
| Active Ingredient | 100.0 |
| Cellulose, microcrystalline | 200.0 |
| Colloidal silicon dioxide | 10.0 |
| Stearic acid | 5.0 |

The components are blended and compressed to form tablets, each weighing 315 mg.

FORMULATION EXAMPLE 3

A dry powder inhaler formulation is prepared containing the following components:

| Ingredient | Weight % |
| --- | --- |
| Active Ingredient | 5 |
| Lactose | 95 |

The active mixture is mixed with the lactose and the mixture is added to a dry powder inhaling appliance.

FORMULATION EXAMPLE 4

Tablets, each containing 100 mg of active ingredient, are prepared as follows:

| Ingredient | Quantity (mg/tablet) |
| --- | --- |
| Active Ingredient | 100.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 190 mg |

The active ingredient, starch and cellulose are passed through a No. 20 mesh U.S. sieve and mixed thoroughly. The solution of polyvinyl-pyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 190 mg.

FORMULATION EXAMPLE 5

Capsules, each containing 100 mg of medicament are made as follows:

| Ingredient | Quantity (mg/capsule) |
| --- | --- |
| Active Ingredient | 100.0 mg |
| Starch | 109.0 mg |
| Magnesium stearate | 1.0 mg |
| Total | 210.0 mg |

The active ingredient, cellulose, starch, an magnesium stearate are blended, passed through a No. 20 mesh U.S. sieve, and filled into hard gelatin capsules in 210 mg quantities.

FORMULATION EXAMPLE 6

Suppositories, each containing 100 mg of active ingredient are made as follows:

| Ingredient | Amount |
| --- | --- |
| Active Ingredient | 100 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

FORMULATION EXAMPLE 7

Suspensions, each containing 100 mg of medicament per 5.0 ml dose are made as follows:

| Ingredient | Amount |
| --- | --- |
| Active Ingredient | 100.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

FORMULATION EXAMPLE 8

| Ingredient | Quantity (mg/capsule) |
| --- | --- |
| Active Ingredient | 100.0 mg |
| Starch | 407.0 mg |
| Magnesium stearate | 3.0 mg |
| Total | 510.0 mg |

The active ingredient, cellulose, starch, and magnesium stearate are blended, passed through a No. 20 mesh U.S. sieve, and filled into hard gelatin capsules in 510 mg quantities.

FORMULATION EXAMPLE 9

An intravenous formulation may be prepared as follows:

| Ingredient | Quantity |
| --- | --- |
| Active Ingredient | 250.0 mg |
| Isotonic saline | 1000 ml |

FORMULATION EXAMPLE 10

A topical formulation may be prepared as follows:

| Ingredient | Quantity |
| --- | --- |
| Active Ingredient | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Utility

The compound of formula I are useful for treating proliferative disorders such as cancers, blood vessel proliferation disorders, fibrotic disorders, auto-immune disorders and acute or chronic rejection of transplanted organs, tissues or cells. These disorders are not necessarily independent. For example, fibrotic disorders may be related to, or overlap with, blood vessel disorders. For example, atherosclerosis (which is characterized herein as a blood vessel disorder) results in the abnormal formation of fibrous tissue. Additionally, the growth of cancer itself may be dependent upon blood vessel proliferation.

Blood vessel proliferation disorders refer to angiogenic and vasculogenic disorders generally resulting in abnormal proliferation of blood vessels. Examples of such disorders include restenosis, retinopathies, and atherosclerosis. The advanced lesions of atherosclerosis result from an excessive inflammatory-proliferative response to an insult to the endothelium and smooth muscle of the artery wall. (Ross R., Nature 362:801–809 (1993)). Part of the response appears to be mediated by PDGF-BB secretion, and activation of PDGF-R in endothelial and smooth muscle cells. Both cell migration and cell proliferation play a role in the formation of atherosclerotic lesions.

Fibrotic disorders are due to the abnormal formation of an extracellular matrix. Examples of fibrotic disorders include hepatic cirrhosis and mesangial proliferative cell disorders. Hepatic cirrhosis is characterized by the increase in extracellular matrix constituents resulting in the formation of a hepatic scar. Hepatic cirrhosis can cause diseases such as cirrhosis of the liver. An increased extracellular matrix resulting in a hepatic scar can also be caused by viral infection such as hepatitis. Lipocytes appear to play a major role in hepatic cirrhosis. Inappropriate PDGF-R activity can stimulate lipocyte proliferation.

Mesangial disorders are brought about by abnormal proliferation of mesangial cells. Mesangial hyper-proliferarive cell disorders include various human renal diseases, such as glomerulonephritis, diabetic nephropathy, malignant nephrosclerosis, thrombotic microangiopathy syndromes, transplant rejection, and glomerulopathies. Cancers can be caused by abnormal growth of different types of cells. A "cancer cell" refers to various types of malignant neoplasms, most of which can invade surrounding tissues and may metastasize to different sites, as defined by Stedman's Medical Dictionary 25th edition (Hensyl ed. 1990). Examples of cancers which may be treated by the present invention include intra-axial brain cancers, ovarian cancers, colon cancers, prostate cancers, lung cancers, Kaposi's sarcoma and skin cancers.

These different types of cancers can be further characterized. For example, intra-axial brain cancers include glioblastoma multiforme, anaplastic astrocytoma, astrocytoma, ependymoma, oligodendroglioma, medulloblastoma, meningioma, sarcoma, hemangioblastoma, and pineal parenchymal.

The formation and spreading of blood vessels, or vasculogenesis and angiogenesis respectively, play important roles in a variety of physiological processes such as embryonic development, wound healing and organ regeneration. They also play a role in cancer development by facilitating vascularization of solid cancers. Thus, cancer growth can be inhibited through different mechanisms such as directly inhibiting the growth of cancer cells and/or inhibiting the growth of cells supporting cancer growth.

Among other types of cancer, ovarian cancer may be treated using the methods of this invention. Epithelial ovarian cancer accounts for nearly 90% of all ovarian tumors and continues to be a highly lethal malignancy. Treatment for advanced ovarian cancer generally includes cytoreductive surgery followed by combination chemotherapy with alkylating agents such as cisplatin and cyclophosphamideo. However, long term survival of advanced ovarian cancer patients is extremely poor, in the range of 10%–20%, principally because of the high incidence of metastatic tumors throughout the peritoneal cavity, and, in some cases, the lymph-nodes. Moreover, chemotherapy with cisplatin carries a potential for renal toxicity and progressive neuropathy.

Treatment of ovarian cancers can be carried out by administering a compound of formula I to the cancer cells themselves or to supporting stromal cells (i.e., the framework upon which a tumor or metastatic lesion grows, including but not limited to connective tissue and vascular endothelial cells), and/or in associated vascular endothelial cells. In view of the localized spread of ovarian cancer throughout the peritoneal cavity, a preferred method of administration, particularly in advanced cases, is by intravenous or intraperitoneal injection.

The compounds described herein can also be used in the treatment of primary intra-axial brain tumors of the glioma family, such as astrocytomas and glioblastomas. Glioblastoma multiforme is the most common and most malignant tumor of astrocytic origin in human adults and accounts for more than half of all primary brain tumors (See, for example, *Cecil Textbook of Medicine*, Wyngaarden, Smith, Bennett (eds) W B Saunders, 1992, p. 2220).

Gliomas have the common property of direct invasive involvement of brain tissue, are fundamentally malignant, and are inevitably fatal. Glioblastoma patients have a median survival time of less than one year even when treated aggressively with a combination of surgery, chemotherapy, and radiotherapy. Unfortunately, successful surgical intervention is extremely rare in view of the difficulty or impossibility of defining the microscopic borders of a glioma within normal brain tissue. Similarly, chemotherapy with alkylating agents has met with very little success, and no more than 10% of glioma patients respond significantly. Radiation therapy has demonstrated some value in controlling the growth of gliomas, but often results in substantial neurologic impairment. Therapy with interferon-$\beta$, in combination with radiotherapy and chemotherapy, has met with some success (DeVita, Hellman, Rosenberg (eds) *Biologic Therapy of Cancer*, J. B. Lippincott, 1991).

In addition to other methods of administration, microcatheter technology may be particularly effective at delivering the compositions of the invention directly to the site of the glioma, thereby achieving immediate localized contact with the cancer and proximate endothelial cells and possibly minimizing potential toxicity associated with more distal intra-arterial delivery.

The compounds of formula I can be administered to a patient alone, or in a pharmaceutical composition comprising the active compound and a carrier or excipient. The compounds also can be prepared as pharmaceutically acceptable salts. Examples of pharmaceutically acceptable salts include acid addition salts such as those containing hydrochloride, sulfate, phosphate, sulfamate, acetate, citrate, lactate, tartrate, methanesulfonate, ethanesulfonate, benzenesulfonate, p-toluenesulfonate, cyclohexylsulfamate and quinate. Such salts can be derived using acids such as hydrochloric acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid and quinic acid.

Pharmaceutically acceptable salts can be prepared by standard techniques. For example, the free base form of the compound is first dissolved in a suitable solvent such as an aqueous or aqueous-alcohol solution, containing the appropriate acid. The salt is then isolated by evaporating the solution. In another example, the salt is prepared by reacting the free base and acid in an organic solvent.

Carriers or excipients can be used to facilitate administration of the compound, for example, to increase the solubility of the compound. Examples of carriers and excipients include calcium carbonate, calcium phosphate, various sugars or types of starch, cellulose derivatives, gelatin, vegetable oils, polyethylene glycols and physiologically compatible solvents.

The compositions can be administered by different routes including intravenously, intraperitoneally, subcutaneously, intramuscularly, orally, topically, or transmucosally. Pharmaceutical preparations for oral use can be obtained, for example by combining the active compounds with solid excipient, optionally grinding a resulting mixture, and processing the mixture of granules, after adding suitable auxiliaries, if desired, to obtain tablets or dragee cores. Suitable excipients include fillers such as sugars, including lactose, sucrose, mannitol, and sorbitol; cellulose preparations such as maize starch, wheat starch, rice starch, potato starch, gelatin, gum tragacanth, methyl cellulose, hydroxypropyl-methyl-cellulose, sodium carboxymethylcellulose, and polyvinylpyrrolidone (PVP). If desired, disintegrating agents may be added, such as the cross-linked polyvinyl pyrrolidone, agar, or alginic acid or a salt thereof such as sodium alginate.

Dragee cores should be provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

If desired, the composition can be administered at short time intervals using a pump to control the time interval or achieve continuously administration. Suitable pumps are commercially available (e.g., the ALZET® pump sold by Alza corporation, and the BARD ambulatory PCA pump sold by Bard MedSystems)

The proper dosage depends on various factors such as the type of disease being treated, the particular composition being used, and the size and physiological condition of the patient. Therapeutically effective doses can be determined using standard techniques. For example, therapeutically effective doses for the compounds described herein can be estimated initially from cell culture and animal models. For example, a dose can be formulated in animal models to achieve a circulating concentration range that initially takes into account various inhibitory concentrations as determined in cell culture assays. The animal model data can be used to more accurately determine useful doses in humans.

Plasma half-life and biodistribution of the drug and metabolites in the plasma, tumors, and major organs can be also be determined to facilitate the selection of drugs most appropriate to inhibit a disorder. Such measurements can be carried out, for example, using HPLC analysis from dissected animals treated with the drug. Compounds that show potent inhibitory activity in the screening assays, but have poor pharmacokinetic characteristics, can be optimized by altering the chemical structure and retesting. In this regard, compounds displaying good pharmacokinetic characteristics can be used as a model.

Toxicity studies can also be carried out by measuring the blood cell composition. For example, toxicity studies can be carried out as follows: 1) the compound is administered to mice (an untreated control mouse should also be used); 2)

blood samples are periodically obtained via the tail vein from one mouse in each treatment group; and 3) the samples are analyzed for red and white blood cell counts, blood cell composition, and the percent of lymphocytes versus polymorphonuclear cells. A comparison of results for each dosing regime with the controls indicates if toxicity is present.

At the termination of each study, further studies can be carried out by sacrificing the animals (preferably, in accordance with the American Veterinary Medical Association guidelines Report of the American Veterinary Medical Assoc. Panel on Euthanasia, *Journal of American Veterinary Medical Assoc.*, 202:229–249, 1993). Representative animals from each treatment group can then be examined by gross necropsy for immediate evidence of metastasis, unusual illness, or toxicity. Gross abnormalities in tissue are noted, and tissues are examined histologically. Compounds causing a reduction in body weight or blood components are less preferred, as are compounds having an adverse effect on major organs. In general, the greater the adverse effect the less preferred the compound.

For the treatment of proliferative disorders, the expected daily dose of a compound of formula I ranges from about 0.001 mg/kg/day to about 2000 mg/kg/day; preferably, from about 0.01 mg/kg/day to about 1000 mg/kg/day, more preferably, from about 1 mg/kg/day to about 1000 mg/kg/day. The average plasma level should be about 0.1 to about 1000 μg/mL, preferably 1 to 800 μg/mL, and most preferably 10 to 500 μg/mL. Plasma levels may be reduced if pharmacological effective concentrations of the drug are achieved at the site of interest. Drugs can be delivered less frequently provided plasma levels of the active moiety are sufficient to maintain therapeutic effectiveness. The frequency of dosing or the amount per dose or both can also be adjusted to increase, decrease or stabilize plasma levels over time as required.

The compounds described herein can be used alone or in combination with other types of treatment for proliferative disorders. For example, various different types of general treatments are currently used to treat different types of cancer patients, such as radiation therapy, ablative or partially ablative surgical procedures or a bone marrow transplant.

The compounds of formula I may also be administered to a mammal with a proliferative disorder before, after or in conjunction with other chemotherapeutic agents or with other therapy intended to modulate or to stimulate the mammal's immune system.

The following synthetic and biological examples are offered to illustrate this invention and are not to be construed in any way as limiting the scope of this invention. Unless otherwise stated, all temperatures are in degrees Celsius.

EXAMPLES

In the examples below, the following abbreviations have the following meanings. If an abbreviation is not defined, it has its generally accepted meaning.

| | | |
|---|---|---|
| DMSO | = | dimethylsulfoxide |
| EDTA | = | ethylenediaminetetraacetic acid |
| FBS | = | fetal bovine serum |
| g | = | grams |
| GLN | = | glutamine |

-continued

| | | |
|---|---|---|
| IP | = | intraperitoneal |
| L | = | liter |
| mg | = | milligram |
| mL | = | milliliter |
| mM | = | millimolar |
| mol | = | mole |
| N | = | normal |
| PBS | = | phosphate buffered saline |
| SRB | = | sulforhodamine B |
| TCA | = | trichloroacetic acid |
| μL | = | microliter |
| μM | = | micromolar |

Example 1

Synthesis of N-(3-Methyl-4trifluoromethylphenyl) 2-Cyano-2-(cyclopropylcarbonyl)acetamide Step A: Preparation of N-(3-Methyl-4-trifluoromethylphenyl) 1-Cyanoacetamide Diisopropylcarbodiimide (16.4 mL, 0.10 mol) is added over 10 minutes while stirring without cooling to a solution of cyanoacetic acid (8.6 g, 0.10 mol) and 3-methyl-4-trifluoromethylaniline (0.10 mol) in 100 mL of tetrahydrofuran. The temperature during the addition ranges from 20° C. to 60° C. The mixture is stirred at room temperature for 16 hours and then filtered. The filtrate is evaporated to dryness and the residue is taken up in 100 mL of ethanol. The mixture is stirred at room temperature for one hour and then filtered, washed with ethanol, then dichloromethane and hexane. The product is dried at 60° C. under reduced pressure for 3 hours to obtain the title intermediate.

Step B: Preparation of N-(3-Methyl-4-trifluoromethylphenyl) 2-Cyano-2-(cyclopropylcarbonyl) acetamide Sodium hydride (0.88 g, 0.03 mol) is added to a suspension of the product from Step A (0.01 mol) in 100 mL of tetrahydrofuran and the mixture is stirred at room temperature for 30 minutes. Cyclopropanecarbonyl chloride (1.3 mL, 0.014 mol) is added over 10 minutes and the mixture is stirred at room temperature for 16 hours. After adding 1 mL of water, the mixture is stirred for 10 minutes and then is acidified with 2N hydrochloric acid. The mixture is extracted with ethyl acetate and the organic phase is dried and evaporated to dryness. The residue is heated in 15 mL of dichloromethane and diluted with diethyl ether to obtain the title compound.

Example A

In vitro Tumor Inhibition

The ability of the compounds of formula I to inhibit tumor cell growth was determined using the assay described in Cory A. H et al., *Cancer Commun.* 3(7):207–12, 1991.

Briefly, the assay is a calorimetric method for determining the number of viable cells in proliferation or chemosensitivity assays.

Human tumor cell lines were propagated under sterile conditions in RPMI 1640 (CellGro) with 105 fetal bovine serum (Gibco BRL), 2 mM L-glutamine, and sodium bicarbonate (complete medium). The cells were then incubated at 37° C. in HEPA-filtered Sterilcult $CO_2$ tissue culture incubators (Forma) with 5% $CO_2$ and 95% hymidity. Each cell line was subcultured weekly or biweekly. Only mycoplasma free cultures were used.

The test compounds (100 μL), dissolved in DMSO (Sigma, cell culture grade) and diluted with complete medium, were added to 96-well plates containing attached cellular monolayers (5000 cells/well in 100 μL). After 4–6 days (37° C., 5% $CO_2$), the monolayers were washed 3 times with complete medium. Antiproliferative effects were assessed with the 3-(4,5-dimethylthiazol-2-yl)-5-(3-carboxymethoxyphenyl)-2-(4-sulfophenyl)-2H-tetrazolium, inner salt (MTS dye) conversion assay. On the day of the assay, the MTS stock solution was warmed from its storage temperature of –20° C. to 37° C. and the cell containing samples wells in the microtiter plates were treated with 40 μL MTS solution. The plates were then incubated for 4 hours at 37° C. to allow for conversion in the liquid-soluble formazan product. The absorbance of formazan in each monolayer was measured at 490 nm on a Coulter microplate reader at 2 and 4 hours after the addition of the MTS solution.

Growth inhibition data are expressed as a percentage of absorbance detected in control wells and is proportional to the number of viable cells in the culture. The $IC_{50}$ values (concentration at which 50% inhibition of tumor cell replication occurs) can then be determined.

The $IC_{50}$ of a compound of formula II (laflunimus) for various tumor types in this assay is shown below:

| Tumor Type | Cell Line Designation | $IC_{50}$* (μM) |
|---|---|---|
| Breast | MCF7 | 13 |
| Central Nervous System | C6 | 12 |
| Colon | SW-620 | 6 |
| Leukemia | CCRF-CEM | 28 |
| Lung | EKVX | 14 |
| Ovary | OVCAR-5 | 13 |

*concentration (μM) associated with 50% inhibition of cell growth

In contrast, lefunomide did not achieve $IC_{50}$ effects in either the SW-620 colon cancer cell line or the OVCAR-5 ovarian cancer cell line. In these cell lines and in these tumor types, laflunimus (compound of formula II) has effects that are different than and cannot be predicted from those of lefunomide.

Example B

In vitro Tumor Inhibition

The compounds of formula I can be tested to determine their ability to inhibit tumor growth using the following growth assay. In this assay, the compounds of formula I are tested for their ability to inhibit anchorage-dependent tumor cell growth using the colorimetric assay described by Skehan, et al., *J. Natl. Cancer Inst.*, 82:1107–1112, 1990. The assay measures protein content of acid-fixed cells using the counterion binding dye sulforhodamine B (SRB, Sigma).

The test compounds are first solubilized in DMSO (Sigma, cell culture grade) or PBS (pH 7.4). The test compounds are then diluted into appropriate growth medium at two-fold the desired final assay concentration.

The test compound (100 AL) is added to 96-well plates containing attached cellular monolayers C6 cells (2000 cells/well in 100 μL). After 4 days (37° C., 5% $CO_2$), the monolayers are washed 3 times with PBS and fixed with 200 μL ice-cold 10% trichloroacetic acid (TCA) (Fisher Scientific), and kept at 4° C. for 60 minutes. The TCA is removed and the fixed monolayers are washed 5 times with tap water and allowed to dry completely at room temperature on absorbent paper. The cellular protein is stained for 10 min with 100 μL 0.4% SRB dissolved in 1% acetic acid. After 5 washes with tap water, the dye is solubilized in 10 mM Tris base (100 μL per well) and absorbance read at 570 nm on a Dynatech plate reader model MR5000. Growth inhibition data are expressed as a percentage of absorbance detected in control wells which are treated with 0.4% DMSO or PBS alone.

Example C

In vivo Tumor Inhibition

In vivo tumor inhibition is measured using a subcutaneous Xenograft model. Mice (BALB/c, nu/nu) are implanted with C6 glioma cells and the ability of compounds of formula I to inhibit tumor growth can be measured.

C6 cells are maintained in Ham's F10 supplemented with 10% fetal bovine serum (FBS) and 2 mM glutamine (GLN). Cells are harvested at or near confluence with 0.05% Trypsin-EDTA and pelleted at 450×g for 10 min. Pellets are resuspended in sterile PBS or media (without FBS) to a particular concentration and the cells are implanted into the hind-flank of mice. Tumor growth is measured over 3 to 6 weeks using venier calipers. Tumor volumes are calculated as a product of length×width×height. The test compounds are solubilized in 50–100 μL vehicle (DMSO) or dissolved in PBS (pH 7.4). The compounds are delivered by IP injection at 15 mg/kg/day. A reduction in tumor volume compared to untreated controls indicates that tumor growth is inhibited.

From the foregoing description, various modifications and changes in the compositions and methods of this invention will occur to those skilled in the art. All such modifications coming within the scope of the appended claims are intended to be included therein.

What is claimed is:

1. A method of treating a mammal having a proliferative disorder comprising administering to said mammal a proliferation-inhibiting amount of a compound of formula II or a tautomeric isomer thereof:

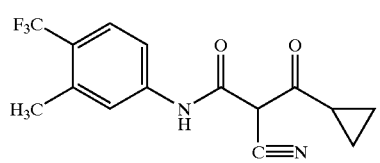

II or a pharmaceutically acceptable salt or pro-drug thereof.

2. A method of inhibiting tumor growth in a mammal having a solid tumor comprising administering to said mammal a tumor growth-inhibiting amount of a compound of formula II or a tautomeric isomer thereof:

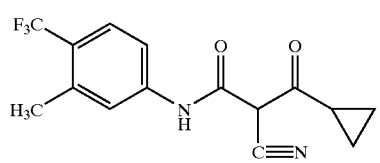

II or a pharmaceutically-acceptable salt or pro-drug thereof.

3. The method of claim 1 wherein the compound of formula II is administered in combination with one or more immunosuppressive agents.

4. The method of claim 3 wherein each immunosuppressive agent is independently selected from the group consisting of azathioprine, corticosteroids, cyclosporin, cyclophosphamide, mycophenolic acid or congeners thereof and monoclonal or polyclonal antibodies.

5. The method of claim 1, wherein the proliferative disorder is cancer.

6. The method of claim 5, wherein the cancer is a solid tumor cancer, a bone marrow cell cancer or lymphatic or a lymph node-related cancer.

7. The method of claim 1, wherein the proliferative disorder is selected from the group consisting of a blood vessel proliferative disorder, fibrotic disorder, and an acute or chronic rejection of a transplanted organ, tissue or cells.

8. The method of claim 1, wherein the proliferation-inhibiting amount of the compound of formula II ranges from about 0.001 mg/kg/day to about 2000 mg/kg/day.

9. The method as in either claim 1 or claim 2, wherein the compound of formula II is administered orally, intravenously, parenterally or transdermally.

10. The method as in either claim 1 or claim 2, wherein the compound of formula II is administered in combination with one or more chemotherapeutic agents.

11. The method of claim 10, wherein each chemotherapeutic agent is independently selected from the group consisting of androgens, asparaginase, azathioprine, 5-azacitidine, BCG, bleomycin, busulfan, carbetimer, carboplatin chlorambucil, cisplatin, corticosteroids, cyclophosphamide, cytarabine, dacarbazine, dactinomicin, daunomycin, doxorubicin, epirubicin, estrogens, etoposide, fadrazole, 5-flurouracil, gemcitabine, hydroxyurea, ifosfamide, interferon alpha, interferon beta, interferon gamma, an interleukin, isotretinoin, lomustine, melphalan, 6-mercaptopurine, methotrexate, mitomycin-c, mitotane, mitoxantrone, paclitaxel, pentostatin, procabazine, progestins, rituximab, streptozocin, tamoxifen, taxotere, teniposide, thioguanine, thiotepa, topotecan, toremifene, tretinoin, uracil mustard, vinblastine, vincristine and vinorelbine.

12. The method as in either claim 1 or claim 2 wherein the compound of formula II is administered in combination with radiation therapy.

13. The method as in either claim 1 or claim 2 wherein the compound of formula II is administered in combination with ablative or partially ablative surgery.

14. A method of treating ovarian cancer in a mammalian patient comprising administering to said patient a proliferation-inhibiting amount of a compound of formula II or a tautomeric isomer thereof:

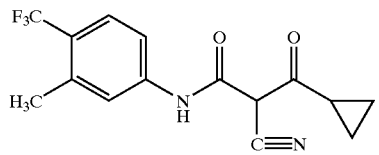

II or a pharmaceutically-acceptable salt or pro-drug thereof; and further wherein the proliferation-inhibiting amount provides a concentration of the compound of formula II in the mammalian patient which treats the ovarian cancer.

15. A method of treating colon cancer in a mammalian patient comprising administering to said patient a proliferation-inhibiting amount of a compound of formula II or a tautomeric isomer thereof:

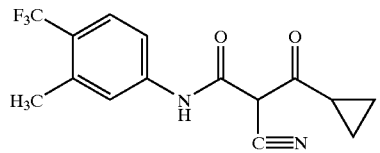

II or a pharmaceutically-acceptable salt or pro-drug thereof; and further wherein the proliferation-inhibiting amount provides a concentration of the compound of formula II in the mammalian patient which treats the colon cancer.

16. A method of treating breast cancer in a mammalian patient comprising administering to said patient a proliferation-inhibiting amount of a compound of formula II or a tautomeric isomer thereof:

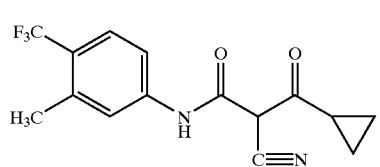

II or a pharmaceutically-acceptable salt or pro-drug thereof; and further wherein the proliferation-inhibiting amount provides a concentration of the compound of formula II in the mammalian patient which treats the breast cancer.

17. A method of treating lung cancer in a mammalian patient comprising administering to said patient a proliferation-inhibiting amount of a compound of formula II or a tautomeric isomer thereof:

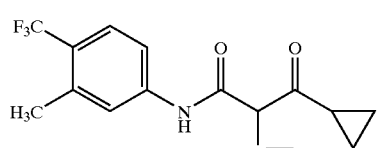

II or a pharmaceutically-acceptable salt or pro-drug thereof; and further wherein the proliferation-inhibiting amount provides a concentration of the compound of formula II in the mammalian patient which treats the lung cancer.

\* \* \* \* \*